US012806336B2

(12) United States Patent
Wine

(10) Patent No.: US 12,806,336 B2
(45) Date of Patent: Nov. 24, 2026

(54) TRANSCUTANEOUS FLUID TRANSFER DEVICE WITH EXPOSURE GUARD

(71) Applicant: CareFusion 303, Inc., San Diego, CA (US)

(72) Inventor: Jason Andrew Wine, Brea, CA (US)

(73) Assignee: CAREFUSION 303, INC., San Diego, CA (US)

( * ) Notice: Subject to any disclaimer, the term of this patent is extended or adjusted under 35 U.S.C. 154(b) by 570 days.

(21) Appl. No.: 18/449,984

(22) Filed: Aug. 15, 2023

(65) Prior Publication Data

US 2025/0058044 A1 Feb. 20, 2025

(51) Int. Cl.
*A61M 5/158* (2006.01)
*A61M 5/162* (2006.01)
*A61M 5/14* (2006.01)

(52) U.S. Cl.
CPC .......... *A61M 5/158* (2013.01); *A61M 5/1626* (2013.01); *A61M 2005/1402* (2013.01)

(58) Field of Classification Search
CPC .............. A61M 5/3146; A61M 5/3271; A61M 2005/3267; A61J 1/201
See application file for complete search history.

(56) References Cited

U.S. PATENT DOCUMENTS 5,125,908 A 6/1992 Cohen
5,591,138 A 1/1997 Vaillancourt
2015/0273161 A1 10/2015 Bengtsson et al.
2021/0128817 A1* 5/2021 Bengtsson .......... A61M 5/3298
2021/0379297 A1* 12/2021 Bengtsson ............ A61M 5/326

OTHER PUBLICATIONS

International Search Report and Written Opinion for Application No. PCT/US2024/034542, dated Sep. 23, 2024, 11 pages.

* cited by examiner

*Primary Examiner* — Laura A Bouchelle
(74) *Attorney, Agent, or Firm* — MASCHOFF BRENNAN

(57) ABSTRACT

A transcutaneous fluid transfer device, a first method of providing a transcutaneous fluid transfer device, and a second method of administering an injection are disclosed. The transcutaneous fluid transfer device includes a first housing, a delivery needle, a second housing, and a plug. The second housing is translatable between a protected position and an injected position and biased toward the protected position. The delivery needle penetrates the plug as the second housing translates toward the injected position. The first method includes providing a first housing and providing a second housing. The second method includes contacting the device to an injection site, translating a second housing, penetrating a plug of the transfer device, advancing a delivery needle, translating the second housing, and sealing the delivery needle. Advantageously, the transcutaneous fluid transfer device may prevent the leakage and/or vaporization of fluids and/or gases from exposed needle tips.

20 Claims, 9 Drawing Sheets

TRANSCUTANEOUS FLUID TRANSFER DEVICE WITH EXPOSURE GUARD

FIELD OF THE INVENTION

The present disclosure generally relates to medical tools and devices and more specifically to medical tools that penetrate the skin for fluid delivery or extraction.

BACKGROUND

Medical tools are used to penetrate the skin for fluid delivery or extraction, such as sharps, needles, syringes, and the like. These tools may be used to pierce the skin of a subject to deliver substances and/or drugs into the muscles, blood vessels, and/or skin of the subject. They may also be used to extract substances from the subject, for example during the performance of phlebotomies or dialysis procedures.

During usage, these tools are often exposed to air and the substances contained therein may escape in their fluid form, or even as gaseous vapors. Patient subjects and medical practitioners may be inadvertently exposed to these substances, which can be potentially hazardous. Healthcare workers, in particular, may use these devices regularly—often multiple times a day—such that exposure to leaks and their detrimental effects may compound over long periods of time.

SUMMARY

One or more embodiments of the present disclosure are directed toward a fluid transfer device including a first housing, a second housing, a biasing mechanism, and a plug. The first housing has a fixedly attached delivery needle. The second housing is longitudinally translatable along a portion of the first housing between a protected position and an injected position. The biasing mechanism biases the second housing toward the protected position. And the plug is attached to a distal end of the second housing. Further, the second housing encapsulates a tip of the delivery needle when the second housing is in the protected position, the tip penetrates the plug as the second housing translates between the protected position and the injected position, and the tip is exposed when the sliding housing is in the injected position.

One or more embodiments of the present disclosure are directed toward a fluid transfer device including a first housing and a second housing. The first housing has a fixedly attached delivery needle. The second housing has a plug at a distal end and is longitudinally translatable along a portion of the first housing between a protected position and an injected position. Further, the second housing is biased toward the protected position, and the needle penetrates the plug as the second housing translates between the protected position and the injected position.

One or more embodiments of the present disclosure are directed toward a method of providing a fluid transfer device. The method includes the steps of providing a first housing having a fixedly attached delivery needle; and providing a second housing having a plug at a distal end, the second housing being longitudinally translatable along a portion of the first housing between a protected position and an injected position. Further, the second housing is biased toward the protected position, and the needle penetrates the plug as the second housing translates between the protected position and the injected position.

One or more embodiments of the present disclosure are directed toward a method of administering an injection using a transcutaneous fluid transfer device. The method includes the steps of contacting a plug of the transfer device to an injection site; translating a second housing of the transfer device from a protected position to an injected position; penetrating a plug of the fluid transfer device with a delivery needle; advancing the delivery needle into the injection site; translating the second housing from the injected position to the protected position; and sealing the delivery needle with the plug.

It is understood that various configurations of the subject technology will become readily apparent to those skilled in the art from the disclosure, wherein various configurations of the subject technology are shown and described by ways of illustration. As will be realized, the subject technology is capable of other and different configurations and its several details are capable of modification in various other respects, all without departing from the scope of the subject technology. Accordingly, the summary, drawings, and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate the disclosed embodiments and together with the description serve to explain the principles of the disclosed embodiments. In the drawings.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Various applications of such embodiments and modifications thereto, which may occur to those who are skilled in the art, are also encompassed by the general concepts described herein.

Figure 1:
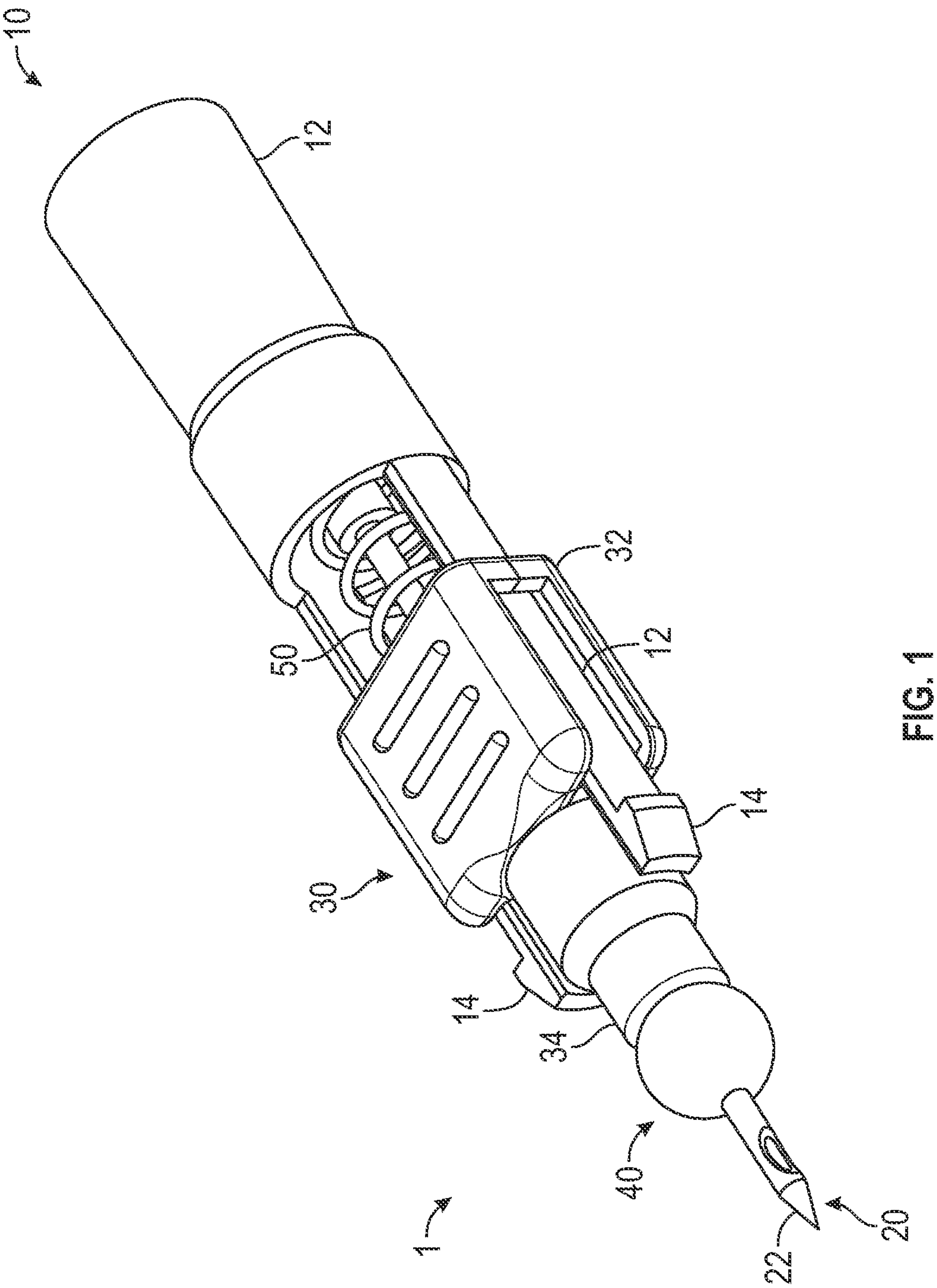
FIG. 1 is a perspective view of a transcutaneous fluid transfer device having a first housing, a second housing in an injected position, a biasing mechanism, and a plug, in accordance with some embodiments of the present disclosure.

Turning now to FIG. 1, a transcutaneous fluid transfer device is generally referred to by a reference numeral 1. The transcutaneous fluid transfer device may include a first housing 10, a second housing 30, a biasing mechanism 50, and a plug 40. The first housing may include a fixedly attached delivery needle 20 having a tip 22. The second housing 30 may be longitudinally translatable along a portion of the first housing 10 between a protected position and an injected position, wherein the biasing mechanism 50 may bias the second housing 30 toward the protected position. The plug 40 may be attached to a distal end 34 of the second housing 30.

Figure 2:
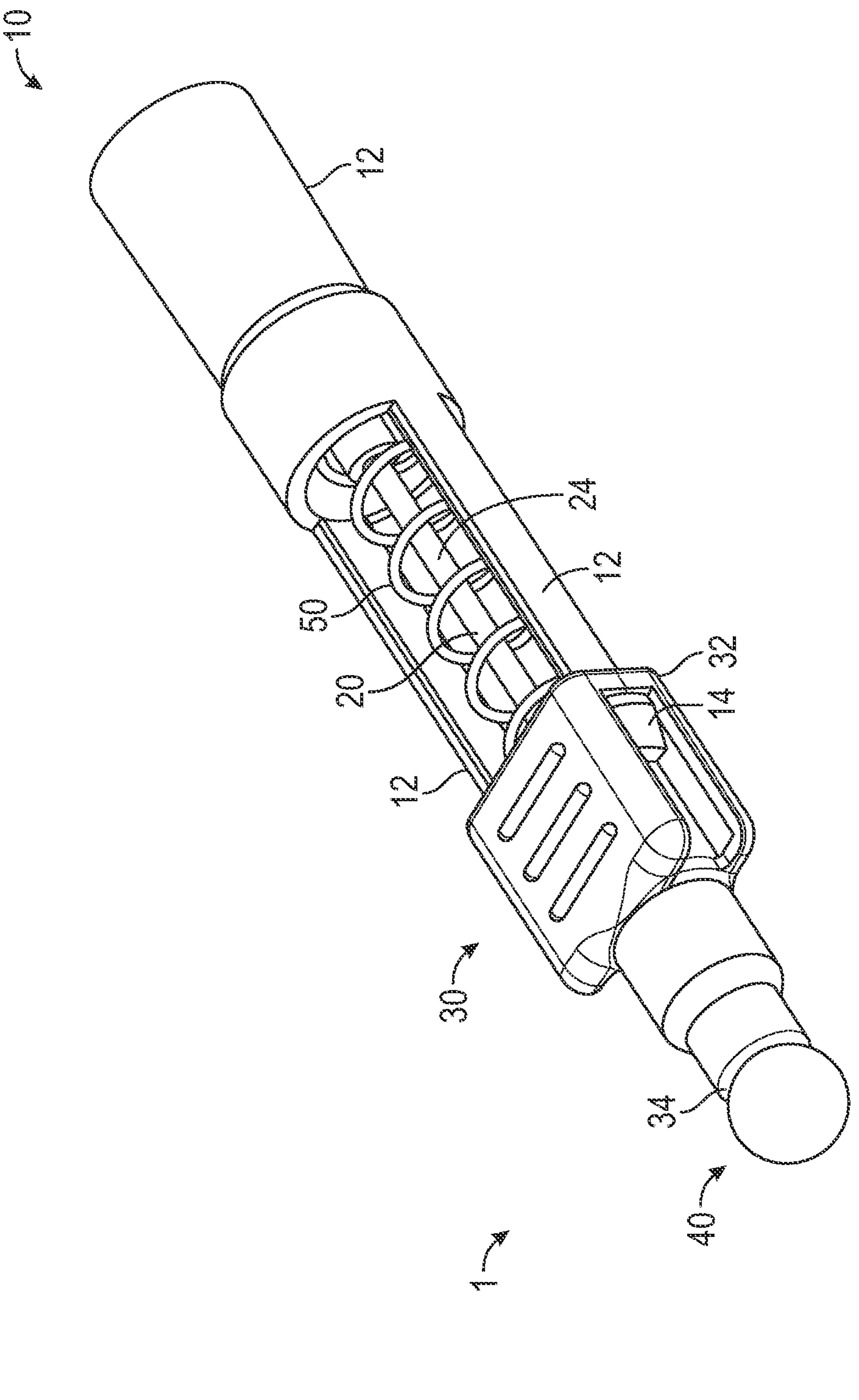
FIG. 2 is a perspective view of a transcutaneous fluid transfer device having a first housing, a second housing in a protected position, a biasing mechanism, and a plug, in accordance with some embodiments of the present disclosure.

FIG. 1 shows the transfer device 1 when the second housing 30 is in the injected position. Turning now to FIG. 2, the same device 1 and components are shown when the second housing 30 is in the protected position. As seen in FIG. 2, when in the protected position, the second housing 30 may encapsulate the tip 22 of the delivery needle 20. Returning to FIG. 1, as the second housing 30 translates between the protected position and the injected the position, the tip 22 may penetrate the plug 40 such that the tip 22 becomes exposed when the second housing 30 is in the injected position.

With continued reference to FIG. 1, in another embodiment of the present disclosure, a transcutaneous fluid transfer device 1 may include a first housing 10 and a second housing 30. The first housing 10 may include a delivery needle 20. In various embodiments, the delivery needle 20 may be fixedly attached to the first housing 10, removably attached to the first housing 10, and/or may be fluidly connected to a core 12 of the first housing 10.

Next, the second housing 30 may include a distal end 34 and a plug 40 at the distal end 34. With reference to both FIG. 1 and FIG. 2, the second housing 30 may be longitudinally translatable along a portion of the first housing 10 between an injected position shown in FIG. 1 and a protected position shown in FIG. 2, and vice versa. Further, the second housing 30 may be biased toward the protected position and the delivery needle 20 may penetrate the plug 40 as the second housing 30 translates between the protected position and the injected position.

With continued reference to FIGS. 1 and 2, in some embodiments the first housing 10 may include a longitudinal rail 12 having a shelf 14 at a distal end and the second housing 30 may include a slot 32 configured to receive the longitudinal rail 12. In an embodiment, the slot 32 may provide a clearance fit for the rail 12 that cannot be cleared by the shelf 14. In the same or other embodiments, an initially free-floating second housing 30 may be attachable to the first housing 10 by inserting the shelf 14 and rail 12 through the slot 32. And in the same or other embodiments, the second housing 30 may be irreversibly attachable. For example, the shelf 14 may be tapered so as to enable the shelf 14 to advance through the slot 32 in a first direction but prevent retraction in the opposite direction. In some embodiments, the first housing 10 may include two longitudinal rails 12 and the second housing 30 may include two slots 32, each configured to receive one rail 12. However, it should be appreciated that other means and designs for longitudinally translating the second housing 30, such as roller tracks or linear bearings, are also possible and envisioned.

With continued reference to FIGS. 1 and 2, in some embodiments the fluid transfer device 1 may further include a biasing mechanism 50 which biases the second housing 30 toward the protected position. In some embodiments, the biasing mechanism 50 may be a spring. For example, the biasing mechanism 50 may be a compression spring having a proximal end pressed against the first housing 10 and a distal end pressed against the second housing 30 and/or the plug 40. In other embodiments, alternative biasing mechanisms are also possible and envisioned, such as but not limited to disc springs, wave springs, and magnetic devices.

Figure 6:
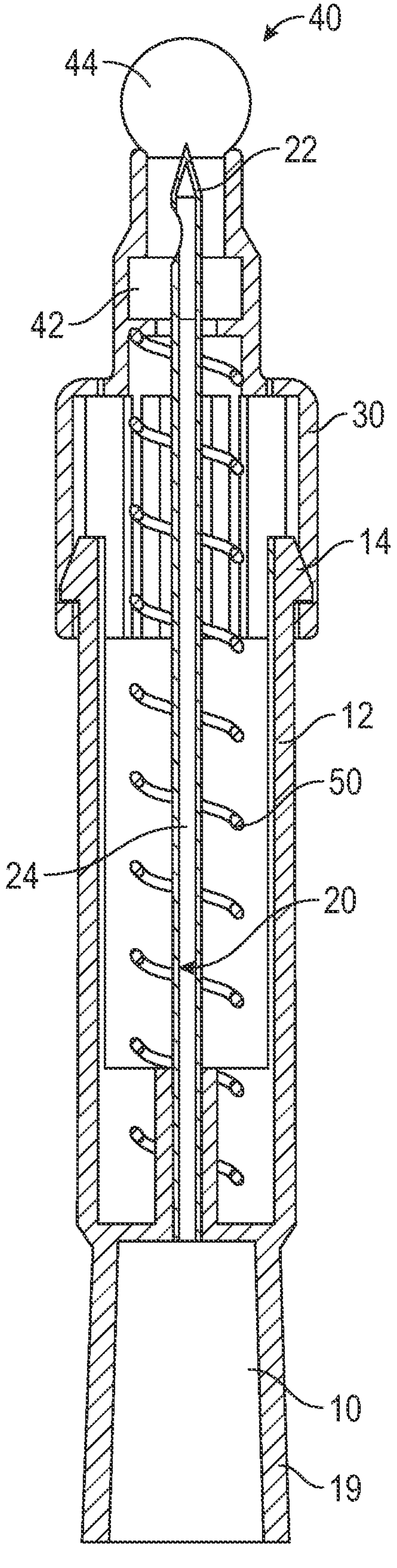
FIG. 6 is a cross-sectional top view of the hypothermic fluid transfer device shown in FIG. 1 in accordance with various aspects of the present disclosure.

Turning now to FIG. 6, a cross-sectional top view of the fluid transfer device 1 is provided. And turning to FIG. 7, a hybrid view displaying the delivery needle 20, plug 40, and a section of the second housing 30 is provided. In both figures, the second housing 30 is shown in the protected position. According to some embodiments, when the second housing 30 is in the protected position, the second housing 30 may encapsulate a tip 22 of the delivery needle 20. For example, the second housing 30 and/or its components may guard against external physical contact with the tip 22. In the same or other embodiments, when the second housing 30 is in the protected position, the plug 40 may encapsulate and seal the tip 22. For example, the plug 40 may prevent fluids or gaseous vapors from entering or exiting the tip 22. In some configurations, the plug 40 may create a hermetic seal of the tip 22. And in other configurations, the plug 40 may seal the tip 22 against liquids only, against specific molecules only, against specific sizes, states, or types of molecules only, or according to other filtering mechanisms known to the art.

Figure 7:
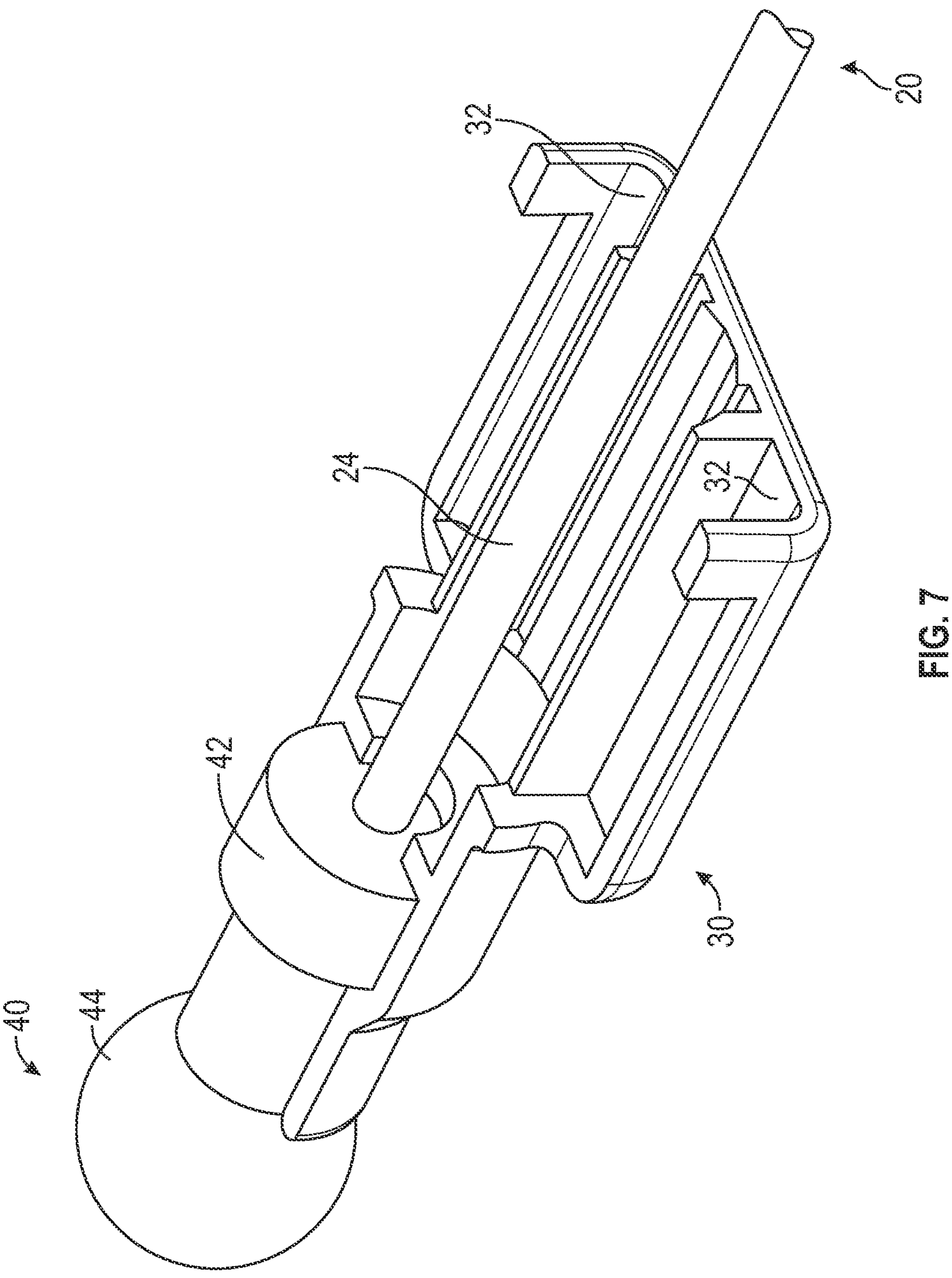
FIG. 7 is a hybrid view displaying a perspective view of the delivery needle and plug, and a sectional view of the second housing in accordance with various aspects of the present disclosure.

As seen in FIG. 6 and FIG. 7, in many embodiments the tip 22 may partially penetrate the plug 40. In other embodiments, however, when the second housing 30 is in the protected position, the tip 22 may sit short of the plug 40 while remaining encapsulated by the second housing 30. Further, various lengths of a shaft 24 of the needle 20 may also be protected by the second housing 30 without departing from the present disclosure.

In some embodiments, the plug 40 may include an enclosed portion 42 and an exposed portion 44. In some configurations of the above, the tip 22 may penetrate only the enclosed portion 42 and, in other configurations, may penetrate both portions 42, 44.

Returning to FIG. 1 and FIG. 2, as the second housing 30 translates distally between the protected position and the injected position, the tip 22 of the needle 20 may fully penetrate the plug (i.e., advance through the plug 40). When the second housing 30 is in the injected position, seen in FIG. 1, the tip 22 of the delivery needle 22 may be exposed. For example, the tip 22 may be exposed to the air, the tip 22 may be accessible to deliver or extract fluids from an injection site, and/or the tip 22 may be accessible to interface with other medical devices or other components of the fluid transfer device 1.

Figure 3:
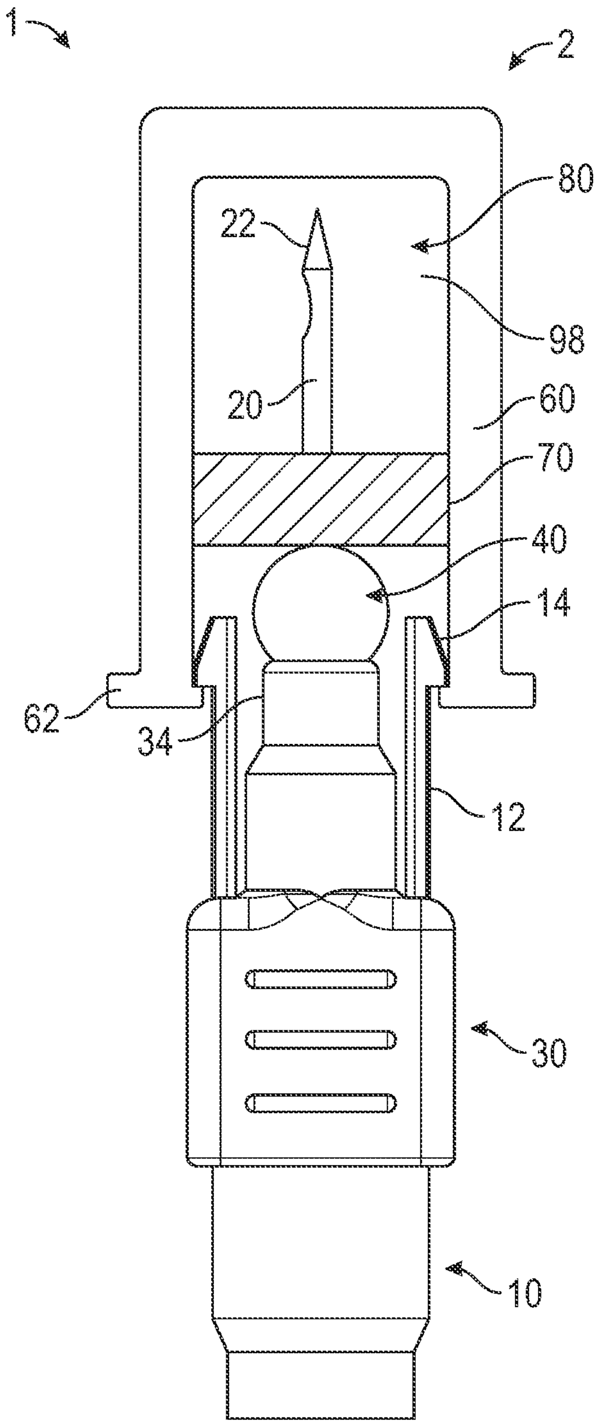
FIG. 3 is a top view of a transcutaneous fluid transfer device having a first housing, a second housing in an injected position, and a priming cap, in accordance with some embodiments of the present disclosure.
Figure 4:
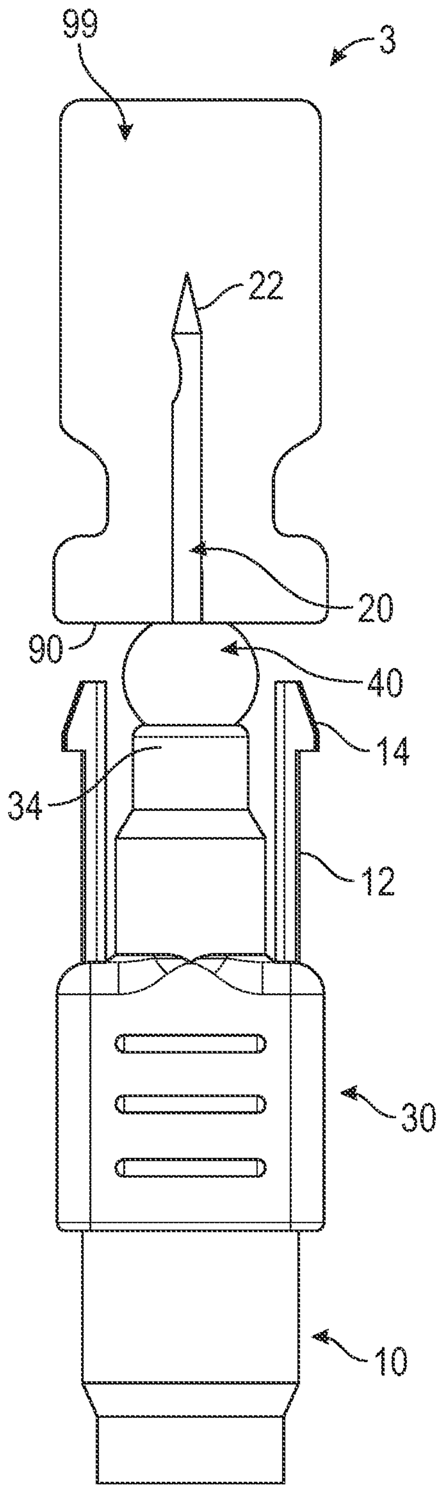
FIG. 4 is a top view of a transcutaneous fluid transfer device having a first housing, a second housing in an injected position, and a drug vial, in accordance with some embodiments of the present disclosure.
Figure 5C:
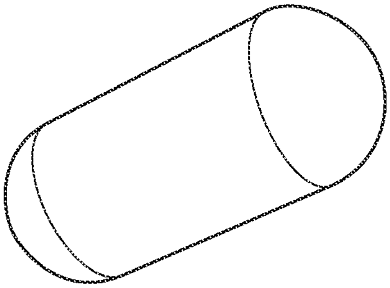
FIG. 5C is a perspective view of a capsule-shaped plug, in accordance with some embodiments of the present disclosure.
Figure 5E:
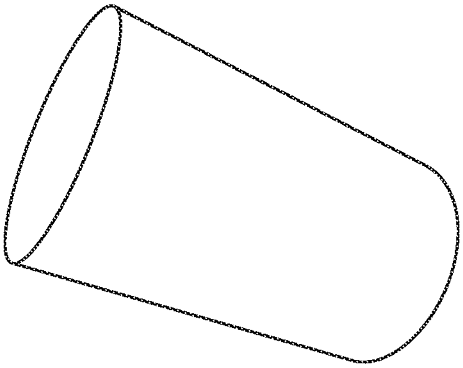
FIG. 5E is a perspective view of a prism-shaped or cylindrical plug, in accordance with some embodiments of the present disclosure.
Figure 5B:
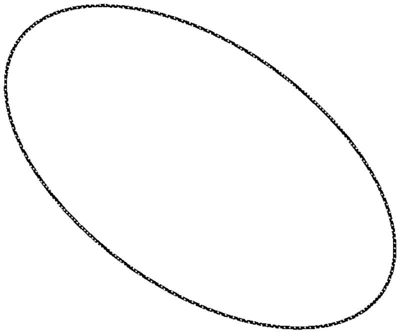
FIG. 5B is a perspective view of an ovoid plug, in accordance with some embodiments of the present disclosure.
Figure 5D:
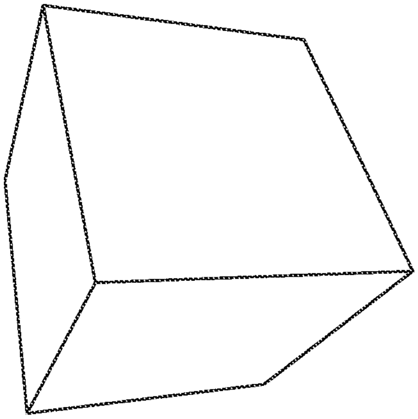
FIG. 5D is a perspective view of a prism-shaped or cuboid plug in accordance with some embodiments of the present disclosure.
Figure 5A:
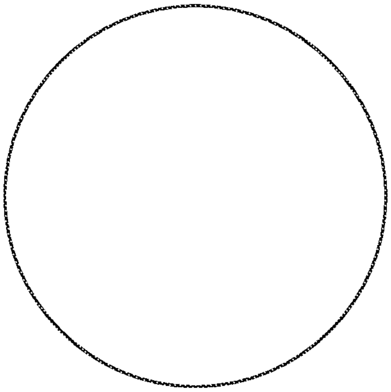
FIG. 5A is a perspective view of a spherical plug, in accordance with some embodiments of the present disclosure.

FIG. 3 shows another such component of the fluid transfer device 1 in the form of a priming cap 2. FIG. 4 shows another such component of the fluid transfer device 1 in the form of a drug vial 3. The priming cap 2 may be used to provide additional protection from or for the needle 20, to further prevent leakage of fluids and/or vapors from the needle 20, to receive fluids from the needle 20 and control an injection dosage, and/or to enable other usages common to the art. The drug vial 3 may store a chemical, drug, tincture, or the like that is intended for injection.

With reference to FIG. 3, in some embodiments, the fluid transfer device 1 may include a priming cap 2 that is removably attached to the first housing 10. The priming cap 2 may further include a cap housing 60 and a cap plug 70, the cap housing 60 and the cap plug 70 creating a sealed interior 80. In some embodiments, the cap housing 60 may further include a lip 62 configured to lock onto the shelf 14 of the first housing 10.

With continued reference to FIG. 3, when the priming cap 2 is attached to the first housing 30, the plug 40 may be in contact with the cap plug 70. Accordingly, as the second housing 30 translates between the protected position and the injected position, the needle 20 may penetrate both the plug 40 and the cap plug 70 before entering the sealed interior 80. The tip 22 may avoid outside exposure entirely and may not be exposed until it reaches the sealed interior 80. In various embodiments, the cap plug 2 may be hermetically sealed, may allow some passage of air, may allow passage of only certain molecule types, or may be sealed at other gradations known to the art. In the same or other embodiments, the priming cap 2 may receive a delivered fluid 98 from the delivery needle 20 and store the fluid in the sealed interior 80. For example, the priming cap 2 may be used to measure and release a drug dosage from the needle 20 prior to an injection. In some embodiments, after the fluid 98 has been deposited in the sealed interior 80, the second housing 30 may be translated back to the protected position. The fluid 98 may then be retained by the cap housing 60 and the cap plug 70 while the needle tip 22 may be sealed by the plug 40.

With reference now to FIG. 4, in some embodiments, the fluid transfer device 1 may include a drug vial 3. The drug vial 3 may include a stored fluid 99 and a pierceable membrane 90. To transfer the fluid 99 from the drug vial 3 to the delivery needle 20, the pierceable membrane 90 may be placed in contact with the plug 40 and the delivery needle 20 may piece the membrane 90 as the second housing 30 translates between the protected position and the injected position. Thus, the tip 22 may avoid outside exposure and may not be exposed until it reaches an interior of the drug vial 3.

Turning now to FIGS. 5A-5E, several different embodiments of the plug 40 are shown. In these and other embodiments, the plug 40 may have different shapes and may be made of different material compositions. For example, the plug 40 may be the spherical plug shown in FIG. 5A, the ovoid plug shown in FIG. 5B, or the capsule-shaped plug shown in FIG. 5C. In some embodiments, the plug may be a prism having a flat contact surface, such as the cuboid plug shown in FIG. 5D or the cylindrical plug shown in FIG. 5E. And in other embodiments, the plug may have an angled contact surface or curved contact surface. It may be understood that the foregoing figures are provided for illustrative purposes only and that many other shapes and geometries of the plug 40 are also possible and envisioned.

In some embodiments, the plug 40 may be made of a self-healing material. For example, the plug 40 may comprise self-healing polymers and microstructures enabling the plug 40 to be repeatedly penetrated by the needle 20 without losing sealing functionality. In some embodiments the plug 40 may be made of polyisoprene. And in those embodiments of the present disclosure including the priming cap 2, the cap plug 70 may be made of the same material as the plug 40 or a different material.

In some embodiments, the plug 40 may be replaceable and may be installed onto and/or removed from the second housing 30. The plug 40 may also be interchangeable in shape and material, such that a replacement plug 40 need not be identical to the one being replaced. In some embodiments, a shape and a material of the plug 40 may be adapted to a type, a location, and an angle of the intended injection. For example, the material of the plug 40 may be selected according to the drug being administered, its hazard level, and its vaporization properties. According to another example, the shape of the plug 40 may be selected such that a contact surface is parallel to or tangential to the angle of injection. And in other embodiments, the shape and material of the plug 40 may be selected according to other injection criteria without departing from the present disclosure.

With reference to FIG. 7, in some embodiments, the plug 40 may include an enclosed portion 42 and an exposed portion 44. The enclosed portion 42 may be enclosed by the distal end 34 of the second housing 30. In some embodiments the enclosed portion 42 and the exposed portion 44 may be made of different materials. For example, the exposed portion 44 may be made of self-healing polyisoprene while the enclosed portion 42 may be made of a material that does not self-heal but whose shape includes a hollow core for the needle 20 to translate through. In the same or other embodiments, the exposed portion 44 may be separable from the enclosed portion 42 and/or replaceable.

Turning now to FIG. 6, in some embodiments, the first housing 10 may include a leak-proof mating mechanism 19. For example, the device 1 may be modular and attachable to other medical tools common to fluid transfer procedures, such as syringes or catheters. In some embodiments, the mating mechanism 19 may be a Luer-Lock fitting.

Figure 9:
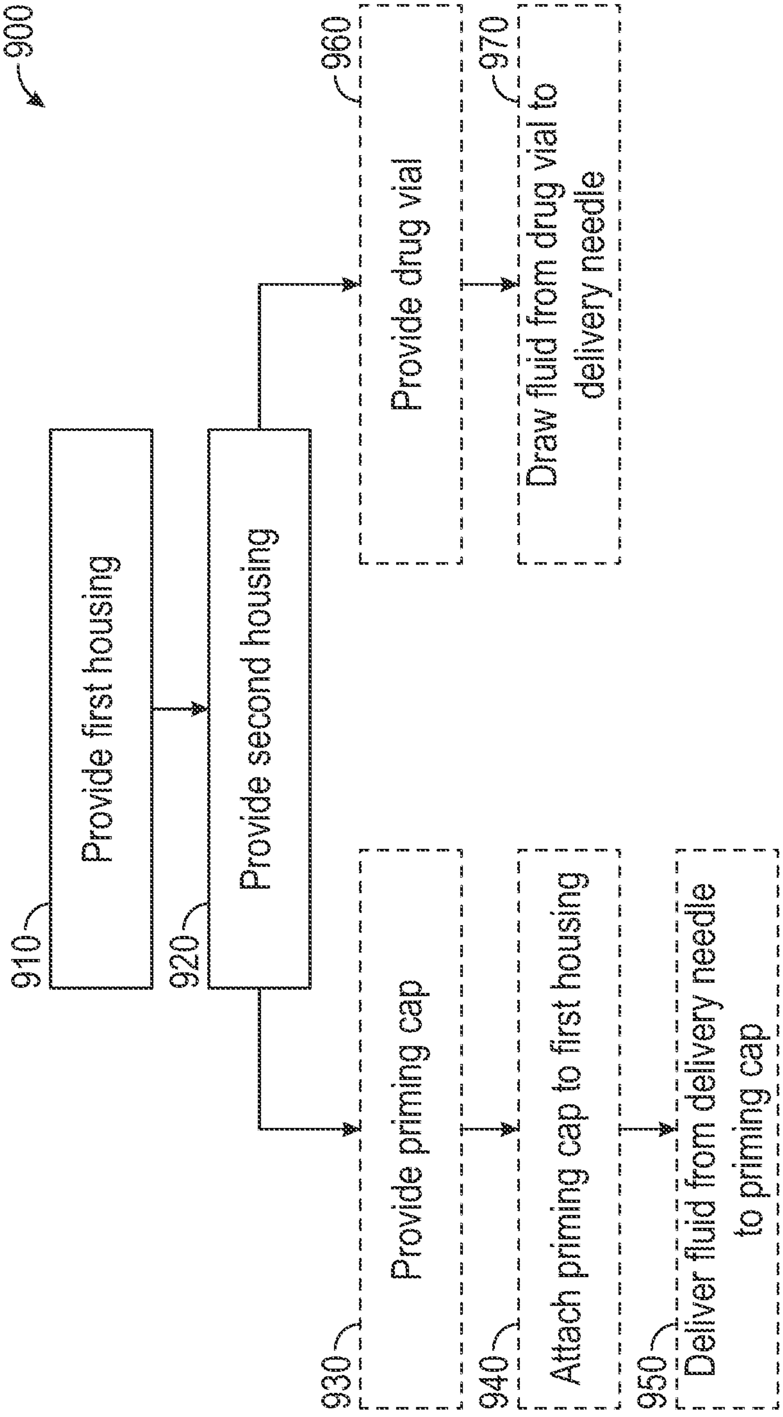
FIG. 9 is a flowchart outlining a second method of providing a transcutaneous fluid transfer device in accordance with various aspects of the present disclosure.

Turning now to FIG. 9, a method of providing a transcutaneous fluid transfer device is outlined and generally referred to by a reference numeral 900. The method 900 may include first providing a first housing (910), the first housing including a fixedly attached delivery needle. Next, the method 900 may include providing a second housing (920), the second housing being longitudinally translatable along a portion of the first housing between a protected position and an injected position. The second housing may be biased toward the protected position, and the needle may penetrate the plug as the second housing translates between the protected position and the injected position.

In some embodiments, the method 900 may further include providing a priming cap (930). The priming cap may include a cap housing and a cap plug, the cap housing and the cap plug creating a sealed interior. Next, the priming cap may be removably attached to the first housing (940), such that the cap plug contacts the plug. In the same or other embodiments, the method 900 may further include delivering a fluid from the delivery needle to the priming cap without exposing a tip of the needle (950). More specifically, this step 950 may include translating the second housing from the protected position to the injected position, and advancing the delivery needle through the cap plug.

In some embodiments, the method 900 may further include providing a drug vial (960). The drug vial may include a pierceable membrane and a stored fluid. In the same or other embodiments, the method 900 may further include drawing the stored fluid from the drug vial to the delivery needle without exposing a tip of the needle (970). More specifically, this step 970 may include contacting the pierceable membrane to the plug, translating the second housing from the protected position to the injected position, advancing the delivery needle through the pierceable membrane, and receiving the fluid into the delivery needle.

It should be appreciated that the steps of the foregoing method 900 may occur in a different order than that illustrated, that one or more steps may be omitted, that one or more steps may be inserted, and that the method 900 may be repeated and/or may be executed in conjunction or concurrence with other methods without departing from a scope of the present disclosure.

Figure 8:
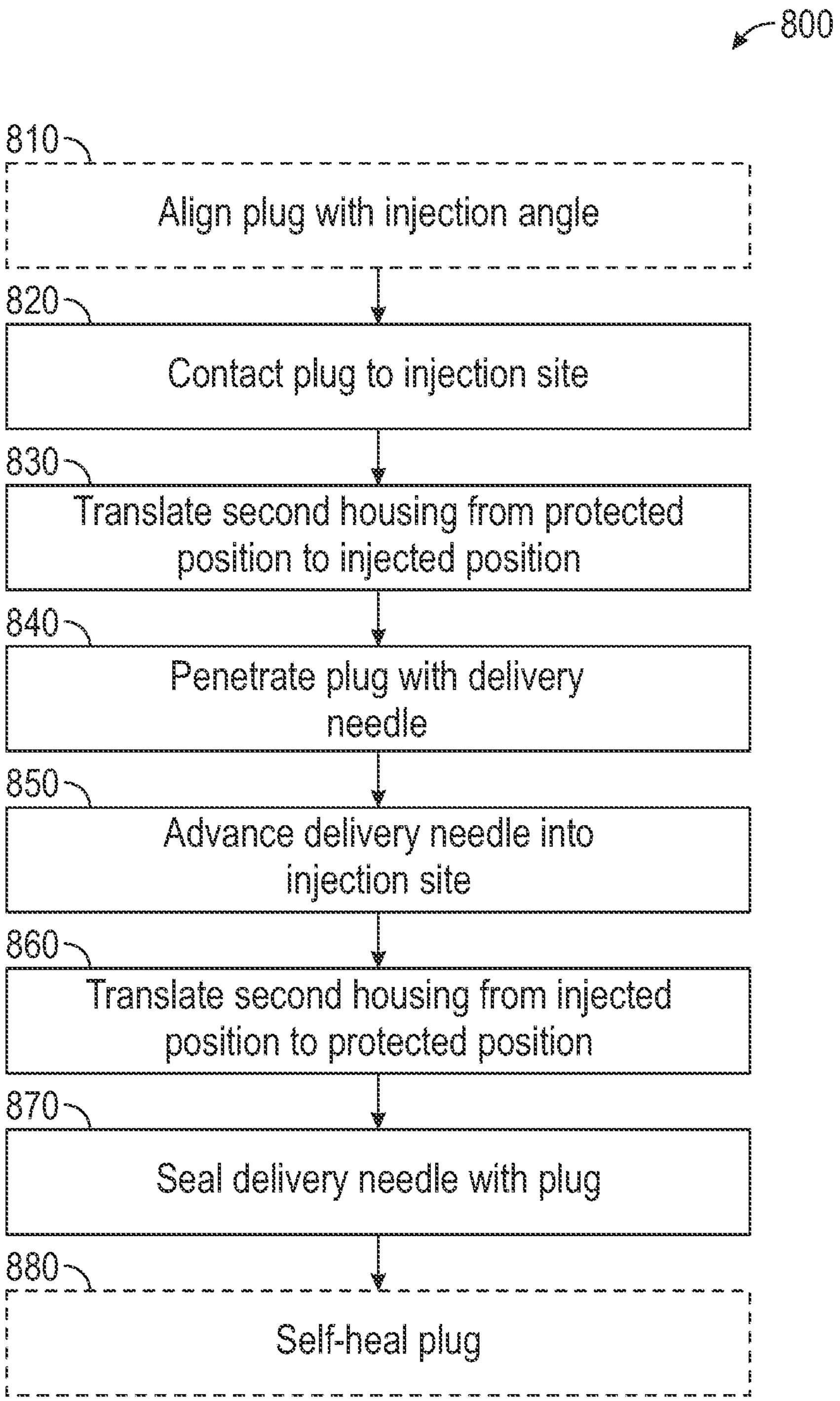
FIG. 8 is a flowchart outlining a first method of administering an injection using a transcutaneous fluid transfer device in accordance with some embodiments of the present disclosure.

Turning now to FIG. 8, a method of administering an injection using a transcutaneous fluid transfer device is generally referred to by a reference numeral 800. The method 800 may include first contacting a plug of the transfer device to an injection site (820). Next, the method 800 may include translating a second housing of the transfer device from a protected position to an injected position (830). Then, a plug of the transfer device may be penetrated with a delivery needle (840), the delivery needle may be advanced into the injection site (850), the second housing may be translated from the injected position to the protected position (860), and the delivery needle may be sealed by the plug (870).

In some embodiments, the method 800 may further include first aligning the plug with an injection angle (810). For example, a shape of the plug may be adapted to an injection type, such as intramuscular, subcutaneous, intravenous, and the like, and a contact surface of the plug may be aligned with the corresponding injection angle. In some embodiments, this step 810 may precede the rest of the administration method 800.

And in the same or other embodiments, the method 800 may further include the plug seal-healing when the second housing is in the protected position (880). In some embodiments, this step 880 may occur subsequent to the rest of the administration method 800.

It should be appreciated that the steps of the foregoing method 800 may occur in a different order than that illustrated, that one or more steps may be omitted, that one or more steps may be inserted, and that the method 800 may be repeated and/or may be executed in conjunction or concurrence with other methods without departing from a scope of the present disclosure.

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

ILLUSTRATION OF SUBJECT TECHNOLOGY AS CLAUSES

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A fluid transfer device, comprising: a first housing comprising a fixedly attached delivery needle; a second housing longitudinally translatable along a portion of the first housing between a protected position and an injected position; a biasing mechanism biasing the second housing toward the protected position; and a plug attached to a distal end of the second housing. Wherein the second housing encapsulates a tip of the delivery needle when the second housing is in the protected position, the tip penetrates the plug as the second housing translates between the protected position and the injected position, and the tip is exposed when the second housing is in the injected position.

Clause 2. A fluid transfer device, comprising: a first housing comprising a fixedly attached delivery needle; and a second housing comprising a plug at a distal end and being longitudinally translatable along a portion of the first housing between a protected position and an injected position. Wherein the second housing is biased toward the protected position, and the needle penetrates the plug as the second housing translates between the protected position and the injected position.

Clause 3. The fluid transfer device of Clause 2, further comprising a biasing mechanism biasing the second housing toward the protected position.

Clause 4. The fluid transfer device of Clause 1 or 3, wherein the biasing mechanism is a spring.

Clause 5. The fluid transfer device of any of Clauses 2 to 4, wherein the second housing encapsulates a tip of the delivery needle when the second housing is in the protected position.

Clause 6. The fluid transfer device of any of Clauses 1 to 5, wherein the plug encapsulates and seals the tip when the second housing is in the protected position.

Clause 7. The fluid transfer device of any of Clauses 2 to 6, wherein a tip of the delivery needle is exposed when the second housing is in the injected position.

Clause 8. The fluid transfer device of any of Clauses 1 to 8, further comprising: a priming cap removably attached to the first housing, the priming cap having a cap housing and a cap plug, the cap housing and the cap plug creating a sealed interior. Wherein the cap plug is in contact with the plug.

Clause 9. The fluid transfer device of Clause 8, wherein the needle penetrates the cap plug as the second housing translates between the protected position and the injected position.

Clause 10. The fluid transfer device of Clause 8 or 9, wherein the priming cap receives a delivered fluid from the delivery needle and stores the delivered fluid in the sealed interior.

Clause 11. The fluid transfer device of any of Clauses 1 to 10, further comprising: a drug vial comprising a stored fluid and a pierceable membrane in contact with the plug, wherein the delivery needle pierces the membrane as the second housing translates between the protected position and the injected position.

Clause 12. The fluid transfer device of any of Clauses 1 to 11, wherein the first housing further comprises a longitudinal rail having a shelf on a distal end; and the second housing further comprises a slot configured to receive the longitudinal rail.

Clause 13. The fluid transfer device of Clause 12, wherein the first housing comprises two longitudinal rails and the second housing comprises two slots, each configured to receive one longitudinal rail.

Clause 14. The fluid transfer device of any of Clauses 1 to 13, wherein the plug is one of spherical, ovoid, and a prism having a flat contact surface.

Clause 15. The fluid transfer device of any of Clauses 1 to 13, wherein the plug comprises an angled flat contact surface.

Clause 16. The fluid transfer device of any of Clauses 1 to 15, wherein the plug further comprises an exposed portion and an enclosed portion, and the exposed portion and the enclosed portion comprise different materials.

Clause 17. A method of providing a hypodermic fluid transfer device, comprising: providing a first housing comprising a fixedly attached delivery needle; and providing a second housing comprising a plug at a distal end, the second housing being longitudinally translatable along a portion of the first housing between a protected position and an injection position. Wherein the second housing is biased toward the protected position, and the needle penetrates the plug as the second housing translates between the protected position and the injected position.

Clause 18. The method of Clause 17, further comprising the steps of: providing a priming cap including a cap housing and a cap plug, the cap housing and the cap plug creating a scaled interior; and removably attaching the priming cap to the first housing such that the cap plug contacts the plug.

Clause 19. The method of Clause 17 or 18, further comprising the step of delivering a fluid from the delivery needle to the priming cap without exposing a tip of the needle, comprising: translating the second housing from the protected position to the injected position; and advancing the delivery needle through the cap plug.

Clause 20. The method of any of Clauses 17 to 19, further comprising: providing a drug vial including a pierceable membrane and a stored fluid; contacting the pierceable membrane to the plug; translating the second housing from the protected position to the injected position; advancing the delivery needle through the pierceable membrane; and receiving the fluid into the delivery needle.

Clause 21. The fluid transfer device of any of Clauses 1 to 13, wherein the plug is replaceable and interchangeable in shape and material.

Clause 22. The fluid transfer device of any of Clauses 1 to 13 and 21, wherein a shape and a material of the plug are adapted to a type, a location, and an angle of an injection.

Clause 23. A method of administering an injection using a hypodermic fluid transfer device comprising the steps of: contacting a plug of the transfer device to an injection site; translating a second housing of the transfer device from a protected position to an injected position; penetrating a plug of hypodermic fluid transfer device with a delivery needle; advancing the delivery needle into the injection site; translating the second housing from the injected position to the protected position; and sealing the delivery needle with the plug.

Clause 24. A fluid transfer device, comprising: a delivery needle; and a housing comprising a proximal portion and a distal portion, the distal portion having a distal end and a plug at the distal end. Wherein the distal portion is longitudinally translatable along a portion of the proximal portion, the distal portion is biased distally, and the delivery needle penetrates the plug as the distal portion translates distally.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neutral gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A fluid transfer device, comprising:

a first housing comprising a fixedly attached delivery needle;

a second housing longitudinally translatable along a portion of the first housing between a protected position and an injected position;

a biasing mechanism biasing the second housing toward the protected position; and a plug attached to a distal end of the second housing, wherein the second housing encapsulates a tip of the delivery needle and the tip is positioned in the plug when the second housing is in the protected position, the tip penetrates the plug as the second housing translates between the protected position and the injected position, and the tip is exposed when the second housing is in the injected position; and a priming cap removably attached to the first housing, the priming cap having a cap housing and a cap plug, the cap housing and the cap plug creating a sealed interior, wherein the cap plug is in contact with the plug.

2. The fluid transfer device of claim 1, wherein the plug encapsulates and seals the tip when the second housing is in the protected position.

3. The fluid transfer device of claim 1, wherein the needle penetrates the cap plug as the second housing translates between the protected position and the injected position.

4. A fluid transfer device, comprising:

a first housing comprising a fixedly attached delivery needle; and a second housing comprising a plug at a distal end and being longitudinally translatable along a portion of the first housing between a protected position and an injected position, wherein the second housing is biased toward the protected position, a tip of the needle is positioned in the plug when the second housing is in the protected position, and the needle penetrates the plug as the second housing translates between the protected position and the injected position; and a priming cap removably attached to the first housing, the priming cap having a cap housing and a cap plug, the cap housing and the cap plug creating a sealed interior, wherein the cap plug is in contact with the plug.

5. The fluid transfer device of claim 4, further comprising a biasing mechanism biasing the second housing toward the protected position.

6. The fluid transfer device of claim 5, wherein the biasing mechanism is a spring.

7. The fluid transfer device of claim 4, wherein the second housing encapsulates the tip of the delivery needle when the second housing is in the protected position.

8. The fluid transfer device of claim 7, wherein the plug encapsulates and seals the tip when the second housing is in the protected position.

9. The fluid transfer device of claim 4, wherein the tip of the delivery needle is exposed when the second housing is in the injected position.

10. The fluid transfer device of claim 2, wherein the needle penetrates the cap plug as the second housing translates between the protected position and the injected position.

11. The fluid transfer device of claim 2, wherein the priming cap receives a delivered fluid from the delivery needle and stores the delivered fluid in the sealed interior.

12. The fluid transfer device of claim 4, further comprising:

a drug vial comprising a stored fluid and a pierceable membrane in contact with the plug, wherein the delivery needle pierces the membrane as the second housing translates between the protected position and the injected position.

13. The fluid transfer device of claim 4, wherein the first housing further comprises a longitudinal rail having a shelf on a distal end; and the second housing further comprises a slot configured to receive the longitudinal rail.

14. The fluid transfer device of claim 13, wherein the first housing comprises two longitudinal rails and the second housing comprises two slots, each configured to receive one longitudinal rail.

15. The fluid transfer device of claim 4, wherein the plug is one of spherical, ovoid, and a prism having a flat contact surface.

16. The fluid transfer device of claim 15, wherein the plug comprises an angled flat contact surface.

17. The fluid transfer device of claim 4, wherein the plug further comprises an exposed portion and an enclosed portion, and the exposed portion and the enclosed portion comprise different materials.

18. A method of providing a hypodermic fluid transfer device, comprising:

providing a first housing comprising a fixedly attached delivery needle; and providing a second housing comprising a plug at a distal end, the second housing being longitudinally translatable along a portion of the first housing between a protected position and an injection position, wherein the second housing is biased toward the protected position, a tip of the needle is positioned in the plug when the second housing is in the protected position, and the needle penetrates the plug as the second housing translates between the protected position and the injected position;

providing a priming cap including a cap housing and a cap plug, the cap housing and the cap plug creating a sealed interior; and removably attaching the priming cap to the first housing such that the cap plug contacts the plug.

19. The method of claim 17, further comprising the step of delivering a fluid from the delivery needle to the priming cap without exposing the tip of the needle, comprising:

translating the second housing from the protected position to the injected position; and advancing the delivery needle through the cap plug.

20. The method of claim 18, further comprising:

providing a drug vial including a pierceable membrane and a stored fluid;

contacting the pierceable membrane to the plug;

translating the second housing from the protected position to the injected position;

advancing the delivery needle through the pierceable membrane; and receiving the fluid into the delivery needle.

* * * * *